United States Patent [19]

Aebischer et al.

[11] Patent Number: 5,182,111
[45] Date of Patent: * Jan. 26, 1993

[54] IN VIVO DELIVERY OF ACTIVE FACTORS BY CO-CULTURED CELL IMPLANTS

[75] Inventors: Patrick Aebischer, Barrington; Shelley R. Winn, Providence, both of R.I.

[73] Assignee: Boston University Research Foundation, Providence, R.I.

[*] Notice: The portion of the term of this patent subsequent to Apr. 21, 2009 has been disclaimed.

[21] Appl. No.: 722,894

[22] Filed: Jun. 28, 1991

Related U.S. Application Data

[63] Continuation-in-part of Ser. No. 369,296, Jun. 21, 1989, abandoned, which is a continuation-in-part of Ser. No. 121,626, Nov. 17, 1987, Pat. No. 4,892,538.

[51] Int. Cl.$^5$ ............... A61F 2/00; A61K 9/22; C12N 11/02
[52] U.S. Cl. ............... 424/424; 424/422; 424/423; 435/177; 435/180; 435/182; 435/240.1; 435/240.2; 435/240.22; 435/284; 530/399; 604/890.1; 604/891.1
[58] Field of Search ............... 424/422–424; 435/177, 240.1, 240.2, 240.22, 180, 182, 284; 604/890.1, 891.1, 93, 36; 623/11, 12; 530/399

[56] References Cited

U.S. PATENT DOCUMENTS

| | | | |
|---|---|---|---|
| 3,093,831 | 6/1963 | Jordan | 3/1 |
| 4,241,187 | 12/1980 | White | 435/284 |
| 4,352,883 | 10/1982 | Lim | 435/178 |
| 4,378,016 | 3/1983 | Loeb | 128/260 |
| 4,391,909 | 7/1983 | Lim | 435/178 |
| 4,402,694 | 9/1983 | Ash et al. | 604/891 |
| 4,686,098 | 8/1987 | Kopchick et al. | 424/424 |
| 4,892,538 | 1/1990 | Aebischer et al. | 604/891.1 |

FOREIGN PATENT DOCUMENTS

0213908 3/1987 European Pat. Off. .
8904655 6/1989 PCT Int'l Appl. .

OTHER PUBLICATIONS

Kordower et al (1987) Annals of the NY Acad. of Sci. 495, 606–605.
Olson et al (1985) Annals of the NY Acad. of Sci. 457, 105–126.
Calne et al. The Lancet, Nov. 8, 1969, pp. 973–976.
Calne et al. (1974) British Med. J. 4:442–444.
Sun et al. (1977) Diabetes 26:1136–1139.
Tresco et al. (1992) *ASAIO Journal* 38:17–23.
Aebischer et al. (1991) *Science* 252:133.
Winn et al. (1991) *Experimental Neurology* 113:322–329.
Aebischer et al. (1991) *Brain Research* 560:43–49.
Aebischer et al. (1991) *J. Biomec. Engineering* 113:178–183.
Aebischer et al. (1991) *Experimental Neurology* 111:269–275.
Aebischer et al. (1991) *Biomaterials* 12:50–56.
Jaeger et al. (1991) *Brain Research* 551:163-170.

(List continue on next page.)

Primary Examiner—Thurman K. Page
Assistant Examiner—G. S. Kishore
Attorney, Agent, or Firm—Thomas J. Engellenner

[57] ABSTRACT

Methods and devices are disclosed for the delivery of an active factor from an implanted co-culture of an active factor-secreting cell obtained from a first source and an augmentary substance-secreting cell obtained from a second source different from the first source, to a target region in a subject. The co-culture is maintained within a biocompatible, semipermeable membrane in which the augmentary substance secreted by the augmentary substance-producing cells stimulates the active factor-producing cells to secrete active factor. The semipermeable membrane permits the diffusion of the active factor therethrough while excluding detrimental agents present in the extenral environment from gaining access to the co-culture.

15 Claims, 4 Drawing Sheets

OTHER PUBLICATIONS

Wells et al. (1987) Annals of the NY Acad. of Sci. 495:804–806.
Aebischer et al. (1988) abstract Soc. of Neurosci. 14:1311.
Aebischer et al. (1988) Brain Res. 448:364–368.
McRae-Dugueurce et al. (1988) Neurosci. Letters 92:303–309.
Rosenberg et al. (1988) Science 242:1575–1578.
Silverman et al. (1987) Annals. of the NY Acad. of Sci. 495:788–791.
Hoffman et al. (1990) *Experimental Neurology 110*:39–44.
Jaeger et al. (1990) *Progress in Brain Research 82*:41–46.
Winn et al. (1989) *Experimental Neurology 105*:244–250.
Winn et al. (1989) *J. Biomed. Mater. Res. 23*:31–44.
Aebischer et al. (1988) *Brain Research 448*:364–368.
Freed et al. (1981) Nature 292:351–352.
Bjorklund et al. (1982) Nature 298:632–634.
Brundin et al. (1985) Exp. Brain Res. 60:204–208.
Hefti et al. (1985) Brain Res. 348:283–288.
Olson et al. (1985) Annals of the NY Acad. of Sci. 457:105–126.
Brundin et al. (1987) Annals of the NY Acad. of Sci. 495:473–496.
Freed et al. (1987) Annals of the NY Acad. of Sci. 495:581–597.
Kordower et al. (1987) Annals of the NY Acad. of Sci. 495:606–622.
Morihisa et al. (1987) Annals of the NY Acad. of Sci. 495:599–605.
Nguyen et al. (1987) Can. J. Physiol. Pharmacol. 65:823–827.
Sagen et al. (1987) Annals of the NY Acad. of Sci. 495:306–333.
Schwartz et al. (1987) Annals of the NY Acad. of Sci. 495–786.

IN VIVO DELIVERY OF ACTIVE FACTORS BY CO-CULTURED CELL IMPLANTS

CROSS-REFERENCE TO RELATED APPLICATIONS

This application is a continuation-in-part of copending U.S. patent application Ser. No. 369,296, filed Jun. 21, 1989, now abandoned, which is a continuation-in-part of U.S. patent application Ser. No. 121,626, filed Nov. 17, 1987, now U.S. Pat. No. 4,892,538.

BACKGROUND OF THE INVENTION

The technical field of this invention is the treatment of active factor deficiency disorders and, in particular, the treatment of diseases and disorders which may be remedied by treatment with active factors, such as neurotransmitters, neuromodulators, hormones, trophic factors, cofactors, and growth factors. All these substances are characterized by the fact they are secreted by "source" cells and produce a specific change in a "target" cell or in the source cell itself.

Deficits in active factors have been implicated in disease with very different phenotypes. For example, lack of neurotransmitter-mediated synaptic contact causes neuropathological symptoms, and can also lead to the ultimate destruction of the neurons involved.

More particularly, paralysis agitans, commonly known as Parkinson's disease, is characterized by a lack of the neurotransmitter, dopamine, within the striatum of the brain, secondary to the destruction of the dopamine secreting cells of the substantia nigra. Affected subjects demonstrate a stooped posture, stiffness and slowness of movement, and rhythmic tremor of limbs, with dementia being often encountered in very advanced stages of the disease.

The direct administration of purified or synthetic dopamine, its precursors, analogs and inhibitors has been studied for therapeutic value in the treatment of Parkinson's disease. These studies have revealed various problems with delivery, stability, dosage, and cytotoxicity of the applied compounds. To date, none of these approaches has demonstrated more than marginal therapeutic value. Brain derived growth factor also may have potential value in the treatment of Parkinson's disease since it has been demonstrated to maintain the viability of striatal neurons in vitro.

Many other deficiency diseases, such as diabetes, myxedema, growth deficiencies and perhaps even Alzheimer's disease, appear to be based in whole or in part on the absence or limited availability of a critical active factor to target cells.

In an attempt to provide a constitutive supply of drugs or other factors to the brain or other organs or tissues at a controlled rate, miniature osmotic pumps have been used. However, limited solubility and stability of certain drugs, as well as reservoir limitations, have restricted the usefulness of this technology. For example, controlled sustained release of dopamine has been attempted by implanting dopamine encapsulated within bioresorbable microcapsules (McRae-Degueurce et al. (1988) Neurosci. Lett. 92:303–309). However, controlled sustained release of a drug from a bioresorbable polymer may rely, e.g., on bulk or surface erosion, which may be due to various hydrolytic events. Erosion often relies on hydrolytic events which increase the likelihood of drug degradation, and complicates establishment of predictable release rates. Other disadvantages associated with pumps and resorbable polymers include finite loading capabilities and the lack of feedback regulation.

The implantation of cells capable of constitutively producing and secreting biologically active factors has also been attempted. Recently, remedial transplantation of neurotransmitter-secreting tissue has been accomplished using the patient's own tissue so as not to elicit an immune response. For example, catecholamine-secreting tissue from the adrenal medulla of patients suffering from Parkinson's disease has been implanted in their striatum with some success. However, this procedure is only used in patients less than 60 years of age, as the adrenal gland of older patients may not contain sufficient dopamine-secreting cells. This restriction limits the usefulness of the procedure as a remedy since the disease most often affects older people.

Other approaches have been attempted to transplant cells into brain tissue even though the brain is considered "immuno-privileged", rejection ultimately occurs with both allografts and xenografts. This problem necessitates the co-administration of immuno-suppressors, the use of which renders their own set of complications and deleterious side-effects.

A number of researchers have proposed the use of microcapsules, i.e., tiny spheres which encapsulate a microscopic droplet of a cell solution, for both therapeutic implantation purposes and large scale production of biological products.

An alternative approach has been macroencapsulation, which typically involves loading cells into hollow fibers and then sealing the extremities. In contrast to microcapsules, macrocapsules offer the advantage of easy retrievability, an important feature in therapeutic implants.

However, there are shortcomings in both the microcapsule and macrocapsule approaches to cell culturing. The viability of encapsulated cells as in vivo implants often fails for as yet undetermined reasons. Even when the cells remain viable, they sometimes secrete their products at lower than therapeutically useful levels.

Therefore, there exists a need for improved therapies for the treatment of active factor deficiency disorders in general and, in particular, a need for therapy devices which can revitalize or replace the functions of dysfunctional areas of the brain or other organs without causing excessive trauma. More specifically, there exists a need for methods of enhancing and/or sustaining the delivery of biologically active factor to a localized region of a subject.

Accordingly, it is an object of the present invention to provide more reliable or more potent, implantable, therapy devices useful for the sustained and controlled delivery of a biologically active factor to a subject, and more particularly, to provide devices which can deliver a biologically active factor, e.g., a neuroactive trophic factor, or growth factor, to a localized region of a tissue or organ in a subject.

SUMMARY OF THE INVENTION

Methods and devices are disclosed herein for the constitutive and controlled delivery of at least one biologically active factor to an organ or tissue of a subject suffering from a deficiency or organ dysfunction. This active factor is provided by a synergistic combination of at least two cell types derived from different populations of cells from separate sources.

In accordance with the method of present invention, a co-culture of at least one active factor-secreting cell obtained from a first source and at least one augmentary substance-producing cell obtained from a second source different from the first source, are encapsulated within a selectively permeable membrane. This membrane protects the co-culture from autoimmune and viral assault while allowing essential nutrients, cellular waste products, and secreted active factor to diffuse therethrough to the local external environment or to the co-culture.

As used herein, "deficient" or "deficiency" refers to the state of an organ or tissue which can be therapeutically altered by the presence of an active factor-producing cell.

"Active factor-producing cell" as used herein refers to any cell which produces and secretes an active factor such as a neurotransmitter, neuromodulator, or catecholamine, growth factor, cofactor, trophic factor, or hormone. These include cells that produce insulin, Factor VIII, trophic factors such as erythropoeitin and growth hormones, biological response modifiers such as lymphokines and cytokines, enzymes, and antibodies from antibody-secreting cells, neurotransmitters, such as enkephalins, dynorphins, Substance P, and endorphins, GABA, glutamic acid, serotonin, dopamine norepinephrine, epinephrine, and acetylcholine, as well as growth factors such as NGF, EGF, PDGF, and an array of fibroblast growth factors, and neurotrophic factors such as BDNF and NT-3. This term also includes any cell which produces and secretes analogs, agonists, derivatives, or fragments of an active factor having the biological activity of the active factor as well as inhibitors of normal biological factors in some instances where disease is caused by an excess of such biological factor (e.g., as in Huntington's Disease). In addition, cells which naturally produce and secrete active factor, as well as those which are genetically engineered to produce active factor, are included.

"Augmentary substance" as used herein includes any molecule produced by an augmentary substance-producing cell which induces another type of cell to produce and secrete active factor and/or enhances the production of active factor, generally. This term also encompasses those molecules which cause cells to grow, proliferate, and/or differentiate into active factor-producing cells. Preferred augmentary substances include growth factors such as nerve growth factor (NGF), fibroblast growth factor (FGF), epidermal growth factor (EGF), platelet derived growth factor (PDGF), trophic factors such as brain-derived neurotropic factor (BDNF), and neurotropin-3 (NT-3), cytokines, lymphokines, and hormones. Other preferred augmentary substances of the invention includes effectors of various membrane receptors such as glutamate or nicotine. The term "augmentary substance" also encompasses not only factors but also agonists, analogs, derivatives, and fragments of an augmentary substance which have the ability to induce cells to secrete active factor and/or stimulates such cells to produce active factors including, for example, recombinantly produced analogs of FGF, EGF, PDGF, NT-3, BDNF, and NGF.

The term "augmentary substance-producing cell" refers to a cell obtained from one source which produces and secretes into the local environment a molecule which induces a different cell obtained from a separate source to synthesize and secrete active factor. In one embodiment of the invention, the augmentary substance-producing cell is one which normally secretes that augmentary substance, such as NGF-producing hippocampal cells or PDGF-producing platelets. In another embodiment, the augmentary substance-producing cell has been genetically engineered to express and secrete that factor (such as the NFG-secreting ratl N.8-21 fibroblast cell line).

The augmentary substance-producing cell and the active factor-producing cell are different types of cells and are isolated from separate sources.

In one embodiment of the invention, the active factor is a neurotransmitter, and the augmentary substance is a neurotransmitter-stimulating factor. For example in one preferred embodiment, the neurotransmitter-secreting cell is one which secretes dopamine such as cells isolated from the adrenal medulla, embryonic ventral mesencephalic tissue, or are neuroblastic cells. In alternative embodiments, the encapsulated cells produce other neurotransmitters such as gamma aminobutyric acid, serotonin, acetylcholine, norepinephrine, epinephrine, glutamic acid, endorphins, enkephalins, dynorphin, or other compounds necessary for normal nerve functions. In this embodiment the augmentary substance-secreting cells are those which secrete NGF, EGF, BDGF, NT-3, PDGF, or the like.

Alternatively, the encapsulated cells of the present invention may secrete an agonist, analog, derivative, or fragment of an active factor or augmentary substance which is biologically active. For example, an embodiment of the invention includes cells which secrete bromocriptine, a dopamine agonist, or cells which secrete L-dopa, a dopamine precursor.

The encapsulated cells of the present invention may be allospecific, or cells obtained from matched tissue of another of the same species. Alternatively, the cells may be xenospecific, or cells obtained from a similar tissue of a different species. However, regardless of their source, the cells to be transplanted form a co-culture consisting of a cell obtained from one source which synthesizes and secretes a desired active factor in which the region or tissue of a subject is deficient, and a second cell obtained from a second source (different than the first source) which synthesizes and secretes augmentary substance.

In one embodiment, the region targeted for implantation of active factor-secreting cells is the brain or other CNS region in the subject, since this is often the site of many neurological deficiencies or disorders. In other embodiments the targeted area may be the liver, pancreas, kidney, or bone marrow, for example.

The terms "selectively permeable" and "semipermeable" are used herein to describe biocompatible membranes which allow the diffusion therethrough of solutes having a molecular weight of up to about 150,000 daltons. The preferred semipermeable membrane materials include polymeric materials selected from the group consisting of acrylic copolymers, polyvinylidene fluoride, polyurethane, polyvinylchloride, polyurethane isocyanates, polyalginate, cellulose acetate, cellulose nitrate, polysulfone, polyvinyl alcohols, polystyrene, polyamide, polymethyl-acrylate, polyacrylonitrile, polyethylene oxide, and/or derivatives, or mixtures thereof.

In one aspect of the invention an encapsulated co-culture of active factor-producing cells and augmentary substance-secreting cells is implanted within a subject and then retrieved when the cells have expired, are no longer functional, or are no longer required to correct the deficiency disorder. Retrieval can be accomplished by means of a biocompatible, nonresorbable guide wire which is attached to the encapsulating membrane.

In another aspect of the present invention, the encapsulating membrane is in the shape of a tube, with its openings being covered by removable plugs or caps. Such a construct enables the easy replacement of either type of cell within the membrane with other like cells by way of the uncovered tube openings after retrieval from the subject via the attached guide wire.

Alternatively, the membrane is in the form of a macrocapsule or microcapsule. These capsules may include an integral tether that extends from the capsule. The tether preferably is of a length sufficient to reach at least from the treatment site to the proximity of the insertion site. The tether may also be a part of the cell capsule itself that extends above the insertion site. Once the vehicle capsule is positioned in the passageway to the treatment site, the tether may then be secured at the insertion site, e.g., by securing the tether to the outer surface of the skull or other bone and its other end proximal to the insertion site by means of surgical staples, biocompatible adhesive, or other methods available and known to those skilled in the art. Following positioning of the capsule at the treatment site, the insertion site may be closed or capped to prevent introduction of extraneous material to the passageway and the treatment site.

The invention will next be described in connection with certain illustrated embodiments. However, it should be clear that various modifications, additions, and subtractions can be made without departing from the spirit or scope of the invention. For example, the present invention should not be read to require, or be limited to, particular cell lines or a particle membrane shape or material described by way of example or illustration.

BRIEF DESCRIPTION OF THE DRAWINGS

The invention itself can be more fully understood from the following description when read together with the accompanying drawings in which.

DETAILED DESCRIPTION OF THE INVENTION

A method for the constitutive delivery of active factor to a localized target region of a subject suffering from an active factor-curable deficiency or dysfunction, and a device for practicing this method, have been devised. The method includes providing active factor producing cells obtained from a first source and providing augmentary substance-secreting cells obtained from a second source different from the first source. These cells are most often of two different cell types. The cells are then encapsulated within a protective, selectively permeable membrane or cell culture device, which is implanted in a target region of a subject. The co-culturing of these two distinct cell types has a synergistic effect on the expression and secretion of active factor by the active factor-producing cell.

The target region may be any part of the subject's anatomy which responds to, and for which increased levels of active factor have therapeutic valid function. This region may be an organ, tissue or any part of a functional body system, such as the nervous system. Nervous system implants will often be within the brain, as it is the source of numerous neurological dysfunctions.

These encapsulated co-cultures may be allospecific, or cells from another of the same species as the subject in which they are to be implanted, or they may be xenospecific, or those from another of a different species. More particularly, they may be derived from a body organ which normally secretes a particular active factor or an augmentary substance in vivo.

For example, useful neurotransmitter-producing cells include those dopamine-secreting cells isolated from the embryonic ventral mesencephalon, neuroblastoid cell lines, or the adrenal medulla. In addition, adrenal chromaffin cells, when isolated from the cortical cells that secrete glucocorticoids, may differentiate into a neuronal phenotype. Extensive neuritic outgrowths from the isolated chromaffin cells is dependent on the presence of NGF and/or other growth factors when maintained in culture. These growth factors may be provided by growth factor-producing cells such as hippocampal cells, platelets, brain tissue and endocrine gland tissue.

In addition, any cell which secretes a processable precursor, analog, derivative, agonist, or fragment having the biological activity of a desired active factor are useful. Such cells include, for example, cells which elicit bromocriptine, L-dopa, preproinsulin, and the like.

Further, any cells which have been genetically engineered to express active factor or augmentary substance, or agonists, precursors, derivatives, analogs, or fragments thereof which have similar active factor or augmentary substance activity, are also useful in practicing this invention (see, e.g., Rosenberg et al. (1988) *Science* 242:1575-1578). Thus, in such an approach, the gene which encodes the augmentary substance or active factor, or the analog or precursor thereof, is either isolated from a native cell line or constructed by DNA manipulation. The gene can then be incorporated into a plasmid, which in turn is transfected into a host cell for expression. The cells which express the active factor or augmentary substance can be grown in vitro until a suitable density is achieved. A portion of the culture is then used to seed the implantable device. See, e.g., Sambrook et al., *Molecular Cloning. A Laboratory Manual*, Cold Spring Harbor Laboratory (1989), herein incorporated by reference for further discussion of cloning vehicles and gene manipulation procedures. Examples of such genetically engineered cell lines include dopamine-producing PC12 cells and NGF-producing ratl N.8-21 fibroblasts.

Cells obtained from tissue sample may be homogeneous, i.e., of the same cell type. Isolation of a homogenous population of cells may be accomplished by separating the cells of the tissue sampled (e.g., by enzymatically digesting intercellular adhesions), and then sorting them on the basis of morphology and/or biological activity. Cells isolated from a homogeneous population of cells in tissue culture need only be cleanly separated from their neighbors and from cellular debris.

Regardless of the source, the augmentary substance-producing cells and the active factor-secreting cells are placed into an implantable, selectively permeable membrane which protects the resulting co-culture from deleterious encounters with viruses and elements of the immune system. Such protection is particularly important for preserving allografts or xenografts which are eventually considered foreign even in the "immuno-priviledged" regions of the body such as the brain. Accordingly, the membrane bars viruses, macrophages, complement, lymphocytes, and, in some embodiments, antibodies from entry while allowing the passage of nutrients, gases, metabolic breakdown products, other solutes, and the neurotransmitter to pass therethrough. Any biocompatible and nonresorbable materials having pores enabling the diffusion of molecules having a molecular weight of up to about 150 kD are useful for practicing the present invention, with acrylic copolymers, polyvinylchloride, polystyrene, polyurethane, polyamide, polymethacrylate, polysulfane, polyacrylate, polyvinylidene fluoride, polyurethane, isocyanate, polyalginate, cellulose acetate, polysulfone, polyvinyl alcohols, polyacrylonitrile, polyethylene oxide, and derivatives, and mixtures thereof being the most preferable.

The cell culture device may take any shape which will accommodate the two types of cells to be encapsulated, and which will not cause undue trauma upon surgical implantation. Useful shapes include a variety of macrocapsules, microcapsules, multicapsules, and multicompartment capsules with split walls.

Figure 1:
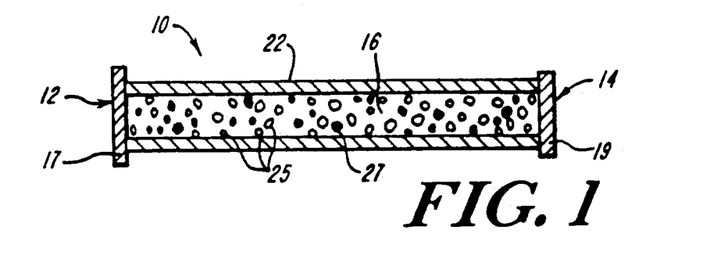
FIG. 1 is a schematic illustration of an implantable co-culture device for delivering active factor, according to one aspect of the present invention.

One preferable implantable co-culture device 10 shown in FIG. 1 is a tubular, selectively permeable membrane 22 having ends 12 and 14 through which active factor-secreting cells 25 and augmentary substance-producing cells 27 are loaded into cell compartment 16. Ends 12 and 14 may then be permanently occluded with caps 17 and 19 or, alternatively, with an epoxy glue or sutures of a biocompatible and nonresorbable material like polypropylene. The device 20 can be surgically implanted into a region of the subject's body such that membrane 22 is in immediate contact with internal tissues or fluids tissues.

Figure 2:
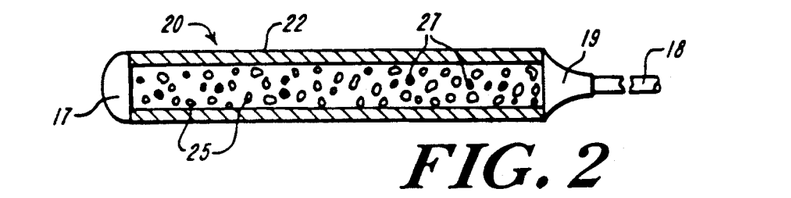
FIG. 2 is a schematic illustration of an implantable and retrievable co-culture device for delivering active factor, according to a second aspect of the invention.

The method of the present invention may include an additional step whereby the initially encapsulated and implanted cells are removed from the subject in the event that they cease to produce active factor or augmentary substance, expire, or are no longer needed to correct the neurological dysfunction. As illustrated in FIG. 2, retrieval of implanted co-culture device 20 is preferably accomplished by means of guide wire 18 which is permanently attached to end cap 17 or 19. This wire may be constructed of any nonresorbable biocompatible material with enough tensile strength to support the cell culture device.

Figure 3:
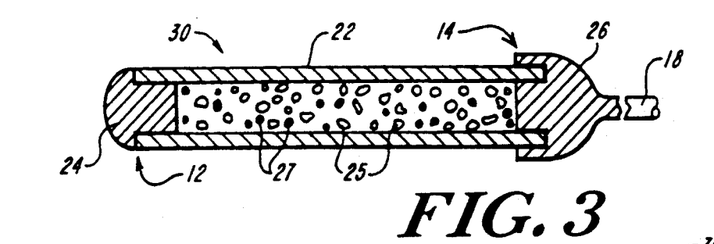
FIG. 3 is a schematic illustration of an implantable, retrievable, and rechargeable co-culture device for delivering active factor, according to another aspect of the invention.

The cellular contents of the device may be replaced in the event that it is desirable to reimplant the device after its retrieval. A exemplary cell culture device 30 useful in practicing this method is shown in FIG. 3. Device 30 is tubular, having ends 12 and 14 reversibly covered with removable, friction-fitted caps 22 and 24, respectively, to enable the extraction and replacement of cells 25 and 27 in cell compartment 16 with new cells. The device 30 can be surgically implanted into the brain of a subject such that guide wire 18 is located directly under the epithelial tissues of the head, and membrane 22 is in immediate contact with brain tissue.

Figure 4:
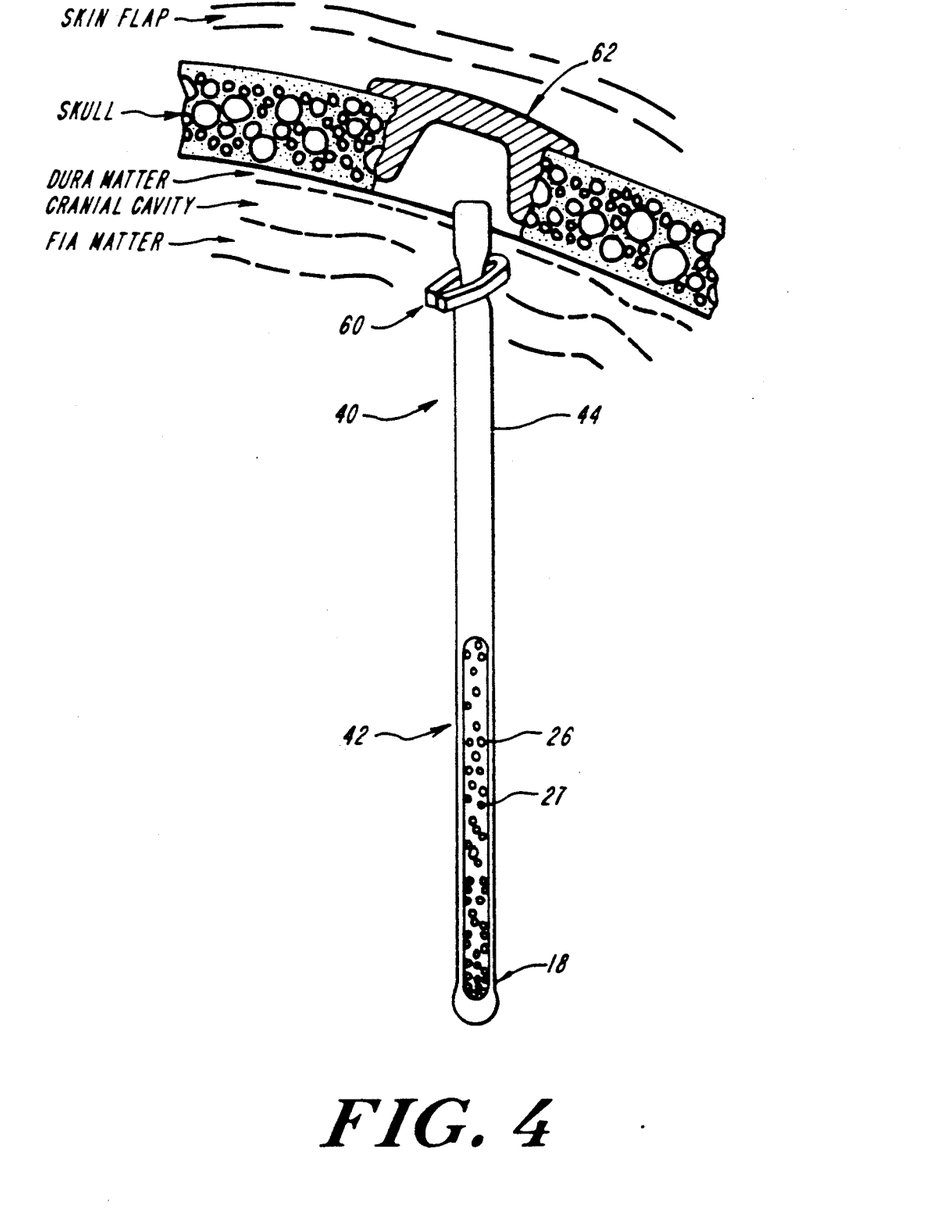
FIG. 4 is a schematic illustration of an implantable co-culture device for delivery of active factor according to yet another aspect of the invention.

Another embodiment of the invention is shown in FIG. 4. The cell culture device 40 includes capsule 42 filled with at least one augmentary substance-producing cell 26 and at least one active factor-secreting cell 27. In a preferred embodiment, the macrocapsule 42 includes a tether 44 or rod extending from and integral with the capsule. The vehicle further includes a permeable, semipermeable, or permselective membrane 18 surrounding the macrocapsule 42. The tether 44 is generally constructed from an impermeable membrane material or may be coated with a material which makes the tether impermeable. In one embodiment, the impermeable protective barrier material may coat a portion of the outer membrane of the capsule. Exemplary protective barrier material includes polyethylene oxides, polypropylene oxides, silicon, hydrogels, and derivatives and mixtures thereof. It should be appreciated that the semipermeable membrane may have alternative shapes that will accommodate the cells such as, for example, a hollow rod, sack, or multiple fibers.

The outer membrane may be a polymer material and may include a surfactant, an anti-inflammatory agent, angiogenic factors, and/or an anti-oxidant. The specific type of polymer, surfactant, or other additive will depend on the material to be encapsulated and the configuration of the extrusion apparatus. Exemplary anti-inflammatory agents include corticoids such as cortisone and ACTH, dexamethasone, cortisol, interleukin-1 (IL-1), and its receptor antagonists, and antibodies to TGF-$\beta$, to IL-1, and to interferon-gamma. Exemplary surfactants include Triton-X 100 (Sigma Chemicals) and Pluronics P65, P32, and P18. Exemplary anti-oxidants include vitamin C (ascorbic acid) and vitamin E.

In the event that the supply of active factor or augmentary substance is spent, (e.g., cells responsible for secreting such factors have expired or are no longer productive, or are no longer needed to correct the particular dysfunction), vehicle 40 can be removed and replaced. Retrieval of implanted vehicle 40 can be accomplished by pulling it out of the treatment site by its tether 44. One way to effect removal is to use a pair of forceps after exposing the tether 44 by removal of the cap 62. Cap 62 may be located directly under the patient's epithelial tissues. The vehicle 40 may be replaced with a new insert in the event that additional therapy is required. Likewise, cells encapsulated within capsule 42 can also be retrieved by removing capsule 42.

The permeable portion (e.g., capsule 42) of vehicle 40 is implanted at or near the target treatment site 12, while the impermeable portion (e.g., tether 42) confines the neuroactive factor to within the boundaries of the insert. The permeable portion includes a polymeric material having pores of a particular size (i.e., having a particular molecular weight cut-off) that excludes some molecules from passage therethrough, while permitting the passage of others. In this way, the diffusion of neurotransmitter from the insert to the treatment site is allowed, while the passage of larger deleterious elements such as viruses, C1q or C3b complement component, and various proteases is effectively barred. For example, vehicles with pores having a molecular weight exclusion of from about 25 kD to about 300 kD are useful, with those having pores with a molecular weight cut off of from about 50 kD to about 200 kD being particularly preferred.

Figure 5:
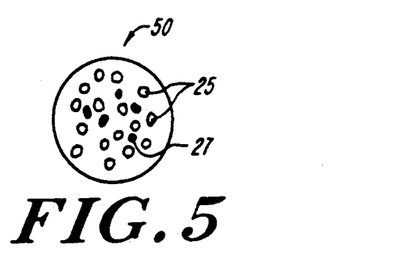
FIG. 5 is a schematic illustration of an implantable, co-culture device including a gel sphere according to another aspect of the invention.
Figure 6:
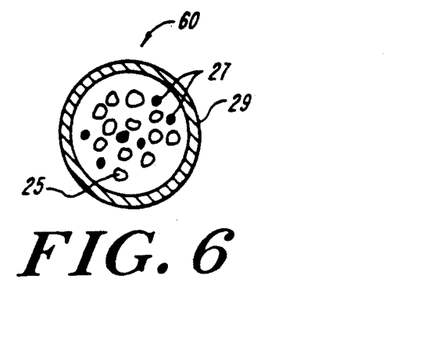
FIG. 6 is a schematic illustration of an implantable, co-culture device including a coated gel sphere according to yet another aspect of the invention.

Other aspects of the invention are shown in FIGS. 5 and 6. In FIG. 5, hydrogel or alginate gel sphere or microcapsule 50 encapsulates the co-culture therein. The gel microcapsule 60 in FIG. 6 is coated with a membrane 29 of, for example, poly-lysine or a thermoplastic material.

Figure 7:
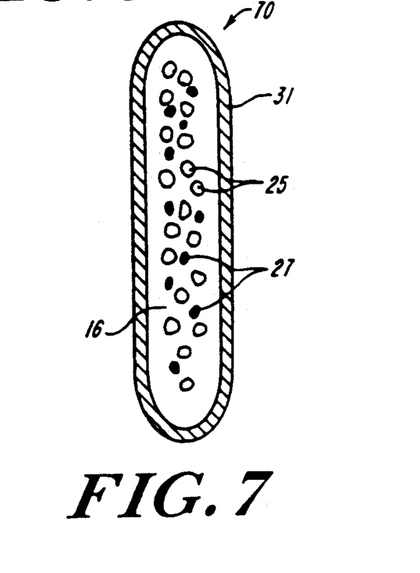
FIG. 7 is a schematic illustration of an implantable co-culture device including a macrocapsule according to another aspect of the invention.
Figure 8:
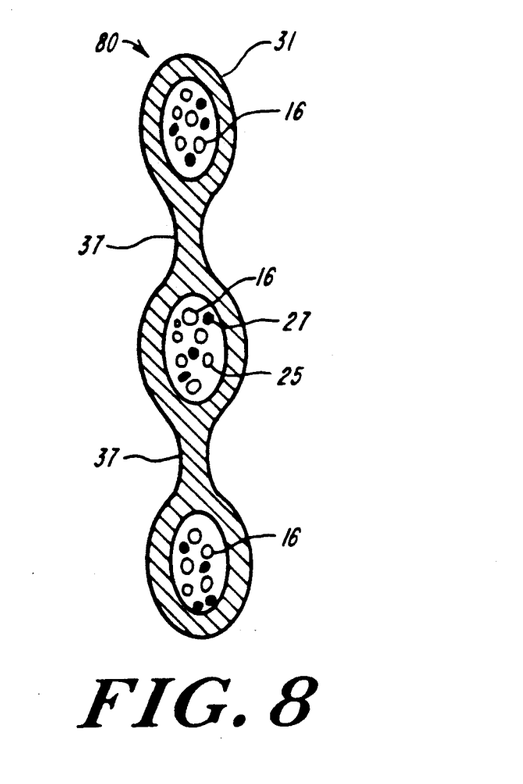
FIG. 8 is a schematic illustration of an implantable co-culture device including several cell compartments according to another aspect of the invention.

The co-culture vehicle alternately may be an extruded macrocapsule 70 shown in FIG. 7 or multimacrocapsule 80 shown in FIG. 8. In these aspects of the invention, cells 25 and 27 are encapsulated within a semipermeable, polymeric membrane 31 by co-extruding an aqueous cell suspension and a polymeric solution through a common port to form a tubular extrudate having a polymeric outer coating 31 which encapsulates the cell suspension.

To prepare such a vehicle, the cell suspension and the polymeric solution may be extruded through a common extrusion port having at least two concentric bores such that the cell suspension is extruded through the inner bore and the polymeric solution is extruded through the outer bore. The polymeric solution coagulates to form an outer coating. As the outer coating is formed, the ends of the tubular extrudate can be sealed at intervals to define a single cell compartment 16 (FIG. 7) or multiple cell compartments 16 connected by polymeric links 37 (FIG. 8).

Figure 9:
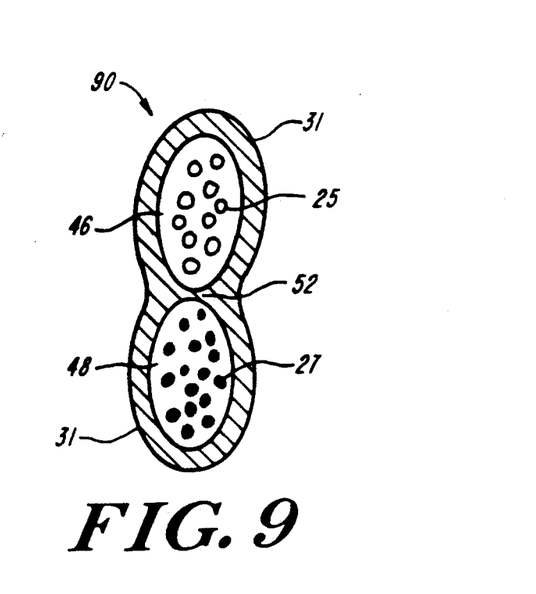
FIG. 9 is a schematic illustration of an implantable, co-culture device comprising a split-wall capsule having two communicating cell compartments according to another embodiment of the invention.

In yet another embodiment of the invention shown in FIG. 9, a vehicle with an internal partition wall 90 encapsulates active factor-secreting cells 25 in a cell compartment 46 separate from cell compartment 48 in which augmentary substance-producing cells 27 are encapsulated. These compartments are separated by, and communicate through, semipermeable membrane 52 through which augmentary substance can diffuse to stimulate active factor-producing cells 25 to secrete active factor.

The following non-limiting examples more fully illustrate preferred features of the invention. These examples describe the ability of a device including a co-culture of isolated chromaffin cells co-seeded with an NGF-releasing cell type encapsulated within selectively permeable microsphere membranes to release the catecholamines dopamine, norepinephrine, and epinephrine. However, this invention is not limited to the cell types described in these examples, nor to the type or shape of selectively permeable membrane system described. For example, extruded macrocapsule devices having one or more cell compartments are included as well as coated and uncoated microcapsules.

EXAMPLE 1

Cellular Preparations

Dissociated bovine adrenal chromaffin cells were isolated as described by Pollard et al. (*J. Biol. Chem.* (1984) 259:1114–22) and Sagen et al (*J. Neurocytol.* (1990) 19:697–707). The cells were maintained in Dulbecco's modified Eagle's medium (DMEM) supplemented with 6% fetal calf serum (FCS) (Gibco, Grand Island Biological Co., Grand Island N.Y.) at 37° C. in a water-saturated, ambient air atmosphere containing 5% $CO_2$. Approximately one week following the isolation procedure, cells were harvested by aspiration, collecting the supernatant and centrifuging at $800 \times g$.

The fibroblast cell line rat1 N.8 was genetically modified through infection with a retroviral vector containing the mouse nerve growth factor (NGF) cDNA (Short et al. (1990) *Devel. Neurosci.* 12:34–45). The clonal line designated rat1 N.8-21 was maintained in DMEM supplemented with 10% FCS and utilized for co-seeding with bovine chromaffin cells after removal from tissue culture flasks by trypsin-EDTA treatment. The rat1 N.8-21 NGF releasing clonal cell line was previously assayed by in ELISA technique and the calculated release of NGF was 165 pg/$10^5$ cells/hour. The NGF released by the rat1 N.8-21 clonal cell line was shown to be biologically active by its ability to induce neuritic extensions in cultured PC12 cells.

EXAMPLE 2

Encapsulation Procedure

Chromaffin cells in 250 μl DMEM were suspended in 800 μl 2% (w/v) isotonic sodium alginate (KelcoGel HV, Kelco, N.J.) at a density of 2, 5, and $10 \times 10^6$/ml designated low, medium, and high, respectively. The co-seeding conditions consisted of $2 \times 10^6$ cells/ml of the rat1 N.8-21 with $3 \times 10^6$ cells/ml chromaffin cells mixed in 250 μl Matrigel ® (Collaborative Research, Lexington, Mass.) suspended in 800 μl 2% isotonic sodium alginate. Matrigel ®, a hydrogel containing laminin (7 mg/ml) and type IV collagen (0.25 mg/ml), was used as a substratum for the fibroblasts. Microbeads of the cellular/alginate suspensions were formed by syringe-pump extrusion and gelled by immersion in a mixing 1.0% $CaCl_2$ solution in physiologic saline at pH 7.4 (5 min). The cell-loaded gelled beads were washed twice with 25 ml of 0.85% NaCl buffered to pH 7.4 with 2.5 mM HEPES (N-2-Hydroxyethylpiperazine-N'-2-ethanesulfonic acid, Sigma, St. Louis, Mo.), and then once in 0.85% NaCl/HEPES pH 8.0. A 0.05% solution of poly-1-lysine (Mw 36-38,000, Sigma) in 0.85% NaCl, pH 7.6, was added to the cell suspended beads and mixed for 6 min. Washes of 0.85% NaCl/HEPES pH 7.4 were followed by immersion in 0.15% sodium alginate for 5 min. The beads were washed in NaCl/HEPES pH 7.4, and an additional layer of poly-1-lysine and alginate was added as described above, prior to exposure of the beads to 50 mM sodium citrate for 5 min to reliquify the entrapped alginate. The microencapsulated chromaffin cells were washed twice in 0.85% NaCl/HEPES pH 7.4 and twice in conditioned culture media before being placed in the incubator.

Approximately 200 cell-loaded microcapsules per well were placed in individual wells of a 24 multiwell tissue culture plate (Falcon 3047). Catecholamine analysis was performed by ion-pair reverse phase high performance liquid chromatography at 1, 4, and 8 weeks on cell-loaded microcapsules maintained in vitro The diameters of 20 microcapsules from each group were measured with a morphometric analysis system (CUE-2, Olympus Corp., Lake Success, N.Y.).

EXAMPLE 3

In Vitro Release Kinetics

Basal and potassium-evoked catecholamine (neurotransmitter) release profiles under static conditions were determined by high performance liquid chromatography (HPLC) with an electrochemical detector (LCEC). Both basal (5.4 mM $K^+$) and potassium-evoked (56 mM $K^+$) release was measured by analyzing 450 $\mu$l 0.29 mM ascorbated HBSS incubations for 15 min each pretreated with 50 $\mu$l of 1.1 N $HClO_4$ prior to column injection. The medium density chromaffin cell-loaded microcapsules and the co-seeded microcapsules were also challenged with 1 mM d-amphetamine sulphate in HBSS under the same conditions after being maintained for 4 and 8 weeks in vitro. The same wells from each group were repeatedly stimulated over time. The HPLC system consisted of a Rabbit TM HPX solvent-delivery system (Rainin Instrument Co. Inc., Woburn, Mass.), reverse-phase-HR-80-column, and a Coulochem multi-electrode electrochemical detector (ESA, Bedford, Mass.) operated at 1.4 ml/min. A 20 $\mu$l aliquot of each sample was injected onto the column. The mobile phase contained 14.2 g/liter monochloroacetate, 37 mg/liter EDTA, 300 mg/liter heptane sulfonic acid and 3% methanol at a pH of 3.0.

The concentration of catecholamines and selected metabolites was determined by comparing the peak heights of serially diluted standards run with each assay. The catecholamine detection limit of the chromatographic system used was 15, 12 and 10 pg for dopamine (DA), epinephrine (EPI), and norepinephrine (NE), respectively.

Two wells from each group were sacrificed at 1, 4 and 8 weeks, and the remaining wells after 12 weeks in vitro, for morphological evaluation. Catecholamine release was expressed as either the average release/well in ng/15 min for statistical purposes or as per capsule (pg/capsule/15 min) obtained by dividing total catecholamine release by the number of microcapsules/-well.

Mean and standard errors of the mean (S.E.M.) were calculated for each time point and group, with the exception of the size distribution of the cell-loaded microcapsules. The paired student t-test was used for statistical analysis.

Figure 10:
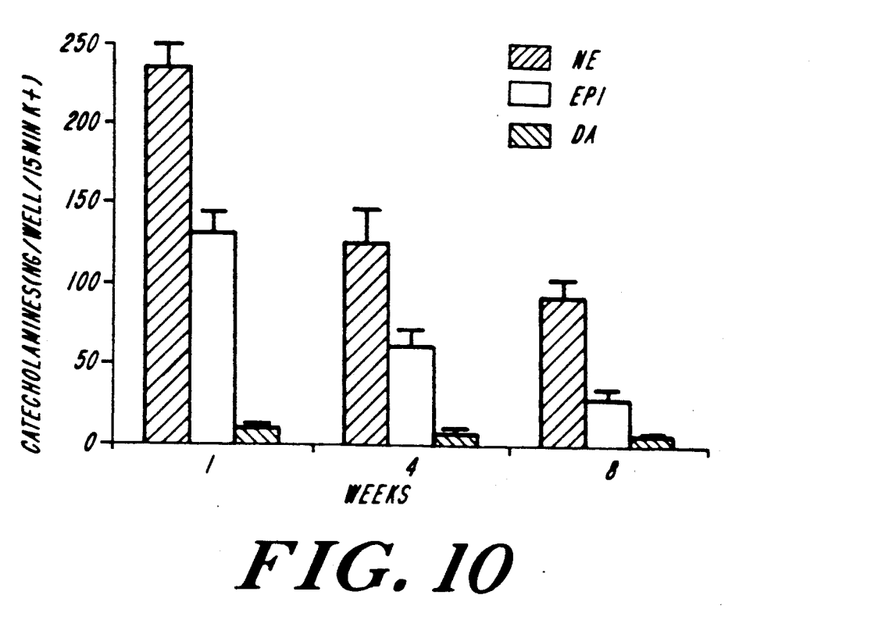
FIG. 10 is a graphic representation of the average potassium-evoked release of neurotransmitters from approximately 200 medium density chromaffin-loaded microcapsules/well after 1, 4, and 8 weeks of maintenance in vitro.
Figure 11:
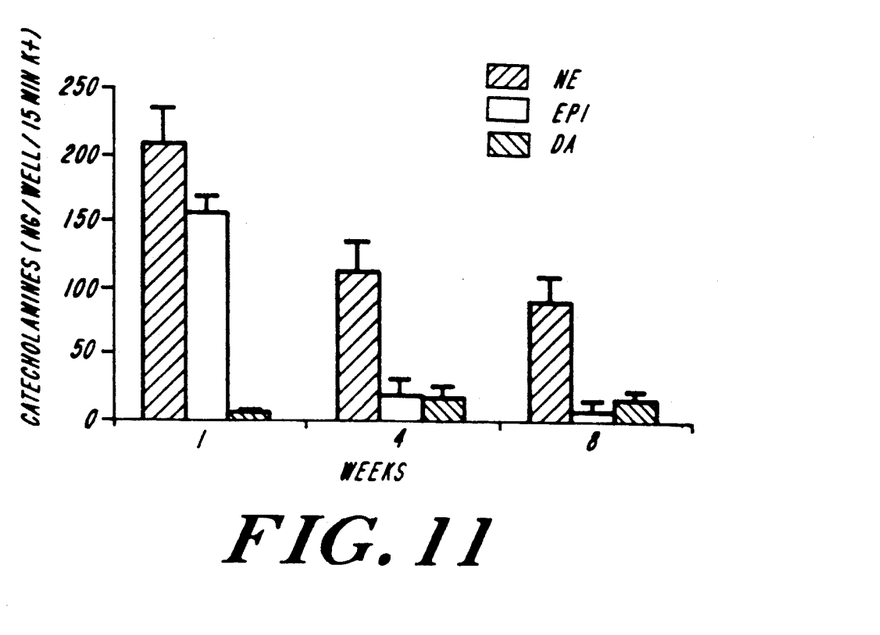
FIG. 11 is a graphic representation of the average potassium-evoked release of neurotransmitters from approximately 300 co-seeded microcapsules/well containing chromaffin and NGF-producing fibroblasts after 1, 4, and 8 weeks of maintenance in vitro.

One week following the encapsulation procedure, the potassium-evoked catecholamine release profile from four wells/group with each well containing approximately 300 microcapsules appeared very similar to that observed with the medium density chromaffin cell loaded microcapsules (FIG. 10). The quantities of NE/-well measured over time decreased in a pattern similar to that which occurred in the medium density chromaffin microcapsules. At 4 weeks, a sharp decrease in the EPI output was seen, in contrast to the medium density chromaffin microcapsules (FIG. 11). By 8 weeks, EPI was detected in only 2 of the 4 wells stimulated with 56 mM $K^+$. A significant increase in the quantity of dopamine released was observed from 1 to 4 weeks in the co-seeded capsules and remained at that elevated level up to 8 weeks in vitro (FIG. 11). Under static incubation conditions, treatment with 1 mM d-amphetamine sulphate induced a significant increase in the output of NE and DA, as compared to basal levels after 8 weeks of maintenance in vitro.

EXAMPLE 4

Morphological Analysis

At selected times microcapsules were fixed in a 4% paraformaldehyde, 0.5% glutaraldehyde solution, rinsed in phosphate buffered saline (PBS), and dehydrated up to 95% ethanol. A 1:1 solution of 95% ethanol and the infiltration solution of glycol methacrylate (Historesin, Reichert-Jung for Cambridge Instruments) was next added to the specimens for 1 hour. Pure infiltration solution replaced the 1:1 mixture and remained for at least 2 hours. The specimens were briefly rinsed with the embedding solution, transferred to flat molds, and embedded in glycol methacrylate. Sections 5 $\mu$m thick were sectioned (Reichert-Jung, Supercut microtome 2050), mounted on glass slides and stained for Nissl substance with cresyl violet. After 4 and 8 weeks in vitro, the relationship and pattern of viability in the medium density chromaffin cell-loaded microcapsules was visualized by simultaneous staining with fluorescein diacetate (FDA) and propidium iodide (PI). One ml suspensions from each time period with approximately 50 cell-loaded microspheres were exposed to working solutions as described by Jones et al. (*J. Histochem, Cytochem,* (1985) 33:77-79). An average of 10 microcapsules/time period were evaluated first for PI (nonviable) and second with FDA (viable) using a epifluorescent microscope (Zeiss IM 35). For ultrastructural observations, microcapsules were fixed in a 3% paraformaldehyde-2% glutaraldehyde overnight, rinsed in 50 mM PBS, and processed as described by Winn et al. (*J. Biomed. Mat. Res.* (1989) 23:31–44). Ultrathin sections were stained with Reynold's lead citrate and uranyl acetate and analyzed with a Phillips 410 transmission electron microscope.

In the co-seeded microcapsules, small neurites were observed at the light microscopic level extending from the chromaffin cells after 4 weeks in vitro. In general, the chromaffin cells and fibroblastic cell line remained isolated from one another. Groups of fibroblasts were also observed after the fourth week of maintenance in vitro. The fibroblasts were observed to be in the vicinity of Matrigel ® within the capsule space. At the ultrastructural level, neuritic extensions from the chromaffin cells were identified, and the fibroblasts continued to survive in the microcapsules after 12 weeks of maintenance in vitro. The fibroblasts were multilayered, aligned along their long-axis, and were identified as the fibroblast cell line on the basis of their cytoplasmic contents.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A cell culture device for implantation within a subject for the delivery of an active factor to said subject, said device comprising:
   a semipermeable membrane permitting the diffusion of an active factor therethrough, while excluding agents present at the site of implantation which are detrimental to cells;
   at least one specific active factor-secreting cell disposed within the membrane, said active factor-secreting cell being isolated from a first tissue or cell line; and
   at least one specific augmentary substance-producing cell disposed within said membrane, said augmentary substance being a molecule which induces the active factor-producing cell to produce active factor, said augmentary substance-secreting cell being isolated from a second tissue or cell line different from said first tissue or cell line, and secreting an augmentary substance that is different from said active factor and that stimulates aid active factor-producing cell to secrete active factor.

2. The device of claim 1 wherein said semipermeable membrane is permeable to solutes having a molecular weight of up to about 150,000 daltons.

3. The device of claim 1 wherein said semipermeable membrane comprises a material selected from the group consisting of polyvinylchloride, polyvinylidene fluoride, polyurethane isocyanates, polyalginate, cellulose acetate, cellulose nitrate, polysulfone, polystyrene, polyurethane, polyvinyl alcohols, polyacrylonitrile, polyamides, polymethylmethacrylate, polyethylene oxide, and mixtures thereof.

4. The device of claim 1 wherein said active factor-producing cell or said augmentary substance-producing cell is allospecific.

5. The device of claim 1 wherein said active factor-producing cell or said augmentary substance-producing cell is xenospecific.

6. The device of claim 1 wherein said active factor-producing cell or said augmentary substance-producing cell or said augmentary substance-producing cell has been genetically engineered to produce said active factor or said augmentary substance.

7. The device of claim 1 wherein said active factor-producing cell is a cell which produces an active factor selected from the group consisting of a neurotransmitter, neuromodulator, growth factor, trophic factor, and hormone.

8. The device of claim 1 wherein said active factor is dopamine, and said active factor-secreting cell is isolated from a tissue or culture selected from the group consisting of adrenal medulla tissue, chromaffin cells, ventral mesencephalic embryonic tissue, neuroblastoid tissue, and a cell genetically engineered to produce dopamine.

9. The device of claim 1 wherein said augmentary substance-producing cell produced an augmentary substance selected from the group consisting of nerve growth factor (NGF), epidermal growth factor (EGF), brain derived neutrophic factor (BDNF), neurotrophin-3 (NT-3), fibroblast growth factor (FGF), platelet-derived growth factor (PDGF), and combinations thereof.

10. The device of claim 1 further comprising a retrievable, nonresorbable, and biocompatible guide wire attached to said semipermeable membrane, so as to enable the removal of said device from said subject.

11. The device of claim 1 wherein said semipermeable membrane is tubular, having at least one end with a removable and reattachable cap element.

12. The device of claim 1 wherein said active factor-secreting cell and said augmentary substance-producing cell are disposed within said semipermeable membrane in a removable fashion, said membrane being tubular, having at least one end with a removable and reattachable cap element, so as to enable extraction of said cells therein.

13. The device of claim 1 wherein said active factor is a neurotransmitter selected from the group consisting of dopamine, norepinephrine, epinephrine, acetylcholine, enkephalins, dynorphin, substance P, gamma aminobutyric acid, glutamic acid, agonists, precursors, analogs, and fragments thereof having neurotransmitter activity.

14. The device of claim 13 wherein said neurotransmitter precursor is L-dopa.

15. The device of claim 13 wherein said neurotransmitter analog is bromocriptine.

UNITED STATES PATENT AND TRADEMARK OFFICE
CERTIFICATE OF CORRECTION

PATENT NO. : 5,182,111

DATED : January 26, 1993

INVENTOR(S) : Aebischer et al.

It is certified that error appears in the above-identified patent and that said Letters Patent is hereby corrected as shown below:

On title page, item [73] Assignee, should read as follows:

--Brown University Research Foundation
Providence, R.I.--

Signed and Sealed this

Twelfth Day of April, 1994

*Attest:*

BRUCE LEHMAN

*Attesting Officer*     *Commissioner of Patents and Trademarks*